(12) United States Patent
Li et al.

(10) Patent No.: US 8,873,037 B2
(45) Date of Patent: Oct. 28, 2014

(54) SERS SUBSTRATES

(76) Inventors: Hao Li, Columbia, MO (US); Mengshi Lin, Columbia, MO (US); Qingsong Yu, Columbia, MO (US)

(*) Notice: Subject to any disclaimer, the term of this patent is extended or adjusted under 35 U.S.C. 154(b) by 178 days.

(21) Appl. No.: 13/106,965

(22) Filed: May 13, 2011

(65) Prior Publication Data

US 2012/0287427 A1 Nov. 15, 2012

(51) Int. Cl.
*G01J 3/44* (2006.01)
*G01N 21/65* (2006.01)
*B82Y 15/00* (2011.01)
*B82Y 20/00* (2011.01)

(52) U.S. Cl.
CPC .............. *B82Y 15/00* (2013.01); *G01N 21/658* (2013.01); *B82Y 20/00* (2013.01)
USPC ........................................................ 356/301

(58) Field of Classification Search
USPC ............... 356/301, 72–73; 977/755, 762, 773
See application file for complete search history.

(56) References Cited

U.S. PATENT DOCUMENTS

| | | | |
|---|---|---|---|
| 6,174,677 B1 | 1/2001 | Vo-Dinh | |
| 2005/0271900 A1 | 12/2005 | Kobrin et al. | |
| 2006/0215154 A1 | 9/2006 | Chan et al. | |
| 2007/0295388 A1* | 12/2007 | Adriani et al. | 136/251 |
| 2009/0159891 A1* | 6/2009 | Daniel et al. | 257/66 |
| 2009/0303472 A1 | 12/2009 | Zhao et al. | |
| 2010/0256016 A1* | 10/2010 | Blair et al. | 506/13 |
| 2012/0081703 A1* | 4/2012 | Moskovits et al. | 356/301 |

* cited by examiner

*Primary Examiner* — Abdullahi Nur
(74) *Attorney, Agent, or Firm* — Brannon Sowers & Cracraft PC; C. John Brannon

(57) ABSTRACT

A surface-enhanced Raman spectroscopy substrate device, including a base substrate, a single or multiple layered nanostructure that contains metals, and a plasma coating. The nanostructure metal is selected from the group including silver, gold, platinum, copper, titanium, chromium, and combinations thereof. The plasma coating has a thickness of 1-200 nm and may locate on the nanostructure layer or on the base substrate. The plasma coating can precisely control the surface characteristics, including surface energy, hydrophilicity, and contact angle, of the SERS device and may then help to regulate the SERS substrate with well defined and uniform water/oil contact angle with small standard deviation. The water contact angle of the SERS substrate may range from 20 to 140 degrees.

9 Claims, 5 Drawing Sheets

SERS SUBSTRATES

TECHNICAL FIELD

The present invention relates generally to materials science, surface engineering, spectroscopy, and, more particularly, surface enhanced Raman spectroscopy (SERS).

BACKGROUND

Optical-based sensing has several major advantages over electronic sensing because optical sensing reveals spectral fingerprints of chemical compounds rapidly and accurately, thus significantly simplifying the detection process and reducing false alarms. One of the most promising optical sensing techniques is surface enhanced Raman spectroscopy (SERS), which employs noble metal nanostructures to dramatically enhance Raman signals. With the aid of metallic nanostructures, such as gold- or silver-based nanosubstrates, a Raman signal can be enhanced by $10^4$ to $10^8$ times or even higher. This enhancement is due to the generation of spatially localized surface Plasmon resonance (SPR) "hot spots" where huge local enhancements of electromagnetic field are obtained. The location of "hot spots" on the metallic structures depends on the geometry of the nanostructures, the excitation wavelength, and polarization of the optical fields. SERS can potentially reach the limit of detection down to the low parts-per-billion (ppb) and theoretically to the single molecule level. Thus, SERS has been increasingly used as a signal transduction mechanism in biological and chemical sensing.

One of the most critical components for surface enhanced Raman spectroscopy (SERS) is the development of suitable substrates that can activate surface plasmon resonance (SPR). In principle, sharp edges of the metal surface topography can produce SPR as induced by an incident excitation laser, thus generating an enormously enhanced electromagnetic field of signals that occur within highly localized optical fields around the metallic structures. When designing a surface structure suitable for SERS application, the size of the metal islands, grains, or particles constructed onto the supporting substrate varies from several nanometers to microns. Generally, a nanoscale structure has multiple advantages over a microscale one because the plasmon localization becomes more intensified at a nanoscale due to a strong spatial confinement effect. As the size of bodies decrease, their surface-to-volume aspect ratios increase. A high surface-to-volume ratio gives rise to an increased number of probe molecules available for capture in the vicinity of metal surface within a distance on the order of nanometers.

Current efforts for nanostructure development can be categorized as either direct or indirect methods. Direct methods involve manipulating the metal directly to prepare a metal substrate with preferred micro- or nanostructures, while indirect methods employ other materials, such as ceramics, to prepare the preferred micro- or nanostructures first and then incorporate the metal onto these structures.

However, there are technical and non-technical challenges in fabrication of SERS substrates that significantly impede the commercial applications of SERS. For example, most existing SERS substrates exhibit inconsistent activities and it is a common problem that a subtle change in the substrate manufacturing process can produce significant changes of the Raman signal. Such inconsistencies make quantitative or even semi-quantitative analysis difficult.

Therefore, there is a need for better SERS substrates with well-controlled surface characteristics to achieve measurement accuracy and consistency in SERS analysis. There is also a need to provide new and improved fabrication method for manufacturing SERS substrates with well-controlled surface characteristics. There is yet another need to develop new and improved SERS analysis protocols for various applications, such as food safety, water safety, homeland security and other areas. The present novel technology addresses these needs.

DETAILED DESCRIPTION

Figure 1A:
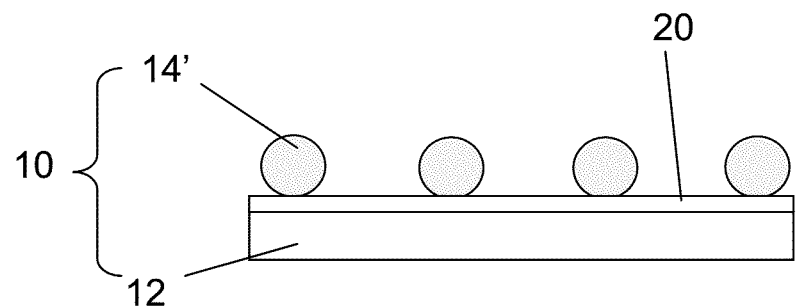
FIG. 1A is a side elevation view of a SERS substrate having a plasma deposition layer between a base substrate and an incomplete metallic nanostructure layer made of SERS active metals, according to one embodiment of the invention.

For the purposes of promoting an understanding of the principles of the invention and presenting its currently understood best mode of operation, reference will now be made to the embodiments illustrated in the drawings and specific language will be used to describe the same. It will nevertheless be understood that no limitation of the scope of the invention is thereby intended, with such alterations and further modifications in the illustrated device and such further applications of the principles of the invention as illustrated therein being contemplated as would normally occur to one skilled in the art to which the invention relates.

The novel technology relates to an improved SERS substrate with well-controlled surface chemistry and surface features, structures, properties, and the like, which give rise to consistent and reliable SERS detection. Specifically, the novel technology relates to the physical and chemical manipulation of the SERS substrate surface to yield control of surface chemical adsorption of analyte molecules, droplet size and solvent evaporation processes. Particularly, a nanoscale thin coating with predetermined surface characteristics, such as surface tension, is applied onto a SERS surface, such as through low temperature plasma deposition techniques. The surface characteristics, such as surface tension, of the nanocoating are adjustable and controllable by manipulating the plasma chemistry or plasma gas composition for the plasma deposition. Particularly, the contact angle with any particular analyte or analyte solution may be precisely controlled over a large range with small special variation (standard deviation). Through the controlled application of such plasma nanocoating, the sampling volume and area on SERS substrates may be kept consistent from spot to spot and/or from substrate to substrate. As a result, consistent chemical absorption of analyte molecules on SERS substrates may be achieved, and reliable and reproducible Raman signals may be detected.

Particularly, the present SERS substrate includes a SERS-active surface that contains nanostructures with SERS-active metals and a plasma coating at least partially deposited upon or beneath the SERS surfaces. The SERS surface may be achieved by direct or indirect methods. The instant novel substrate may feature zero-dimensional, one-dimensional, or two-dimensional surface nanostructures. The novel substrate may include any roughened surfaces, nanoparticles, nanoaggregates, nanopores/nanodisks, nanorods, nanowires, and/or a combination thereof, as well as microstructures, such as a silver-coated microarray and/or a gold-coated microarray. The novel substrates may include multiple layered micro and nano-structures made of SERS active metals. The interaction within and between layers of micro and nanostructures may create more hot spots for SERS enhancement.

According to one embodiment of the present novel technology, the SERS surface may include a base substrate and a metallic nanostructure layer deposited upon the base substrate. As shown in FIG. 1A, the novel SERS substrate 10 may include a base substrate 12 and a metal nanostructure layer 14' as well as a plasma coating layer 20 deposited at least partially upon the base substrate 12. The nanostructure layer 14' is deposited upon the plasma layer 20. The nanomaterial employed in the nanostructure layer 14' may be any SERS-active metallic material, such as silver, gold, copper, platinum, titanium, chromium, combinations thereof or the like. In addition, the nanostructure layer 14' may assume any form, such as nanoparticles, nanoaggregates, nanopores/nanodisks, nanorods, nanowires, or combinations thereof. The substrate 12 may be any ceramic, polymer, or metal materials that are flat and may also provide sufficient mechanical support, such as silicon, quartz (crystalline silica), glass, zinc oxide, alumina, Paraffin film, polycarbonate (PC), combinations thereof and the like. Typically, the substrate 12 materials are generally inert and do not react with analyte and interfere with SERS detection. More typically, the substrate 12 materials have simple Raman spectra with few peaks. The plasma coating layer 20 is typically deposited from low-temperature gas plasmas with thickness in nanoscale (a few to a few hundred nanometers). The surface chemistry and surface energy of the plasma coating layer 20 may be controlled and adjusted by plasma gas selection. The plasma gases for depositing plasma coating layer 20 are typically gases or vapors of silicon-carbons, hydrocarbons, fluorocarbons, mixtures thereof, and their mixtures with simple gases such as oxygen, nitrogen, air, nitrous oxide, ammonia, carbon dioxide, water vapor, argon, helium, mixtures thereof, and the like. The plasma may be produced at a reduced pressure or at one atmospheric pressure by various plasma sources of, but not limited to, direct current, alternating current, audio-frequency, radio-frequency power sources with both a continuous wave and pulsed wave.

Figure 1B:
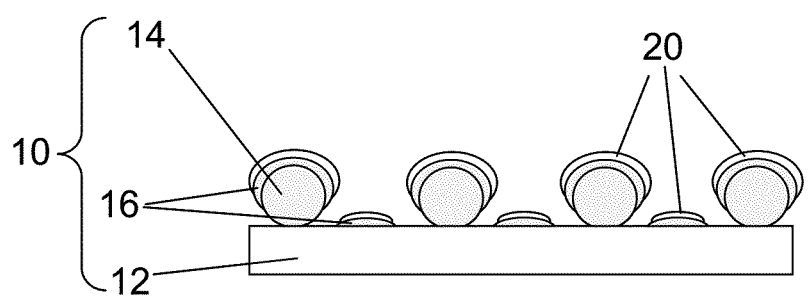
FIG. 1B is a side elevation view of a SERS substrate with a metallic coating layer deposited upon a layer of nanostructures, with additional plasma coating deposited upon the metallic coating layer, according to a second embodiment of the invention.

According to another embodiment of the present novel technology, a novel SERS substrate 10 may include a base substrate 12, a nanostructure layer 14, a metallic coating 16, and a plasma coating layer 20. FIG. 1B is an illustration of one exemplary setup of the embodiment. As shown in FIG. 1B, the SERS substrate 10 is formed on a base substrate 12 with a nanostructure layer 14 and a metallic coating layer 16 whereas the nanostructure layer 14 is deposited upon the base substrate 12 and the metallic coating layer 16 is deposited upon the nanostructure layer 14. A plasma layer 20 is deposited upon the metallic coating layer 16. The nanostructure layer 14 may assume any form, such as nanoparticles, nanoaggregates, nanopores/nanodisks, nanorods, nanowires, or combinations thereof. The materials employed in the nanostructure layer 14 may be any ceramic, polymer, and metal materials. The metallic coating layer 16 may be a thin film with uniform thickness, be a thin film of certain nanoroughness, or be composed of smaller nanostructures, such as nanoparticles. The materials of employed in the metallic layer 16 may be any SERS-active metallic material, such as silver, gold, copper, platinum, titanium, chromium, combinations thereof or the like. The substrate 12 may be any of the ceramic, polymer, or metal materials as described above regarding FIG. 1A, and the plasma coating layer 20 may be any of the materials described above regarding FIG. 1A.

Figure 1C:
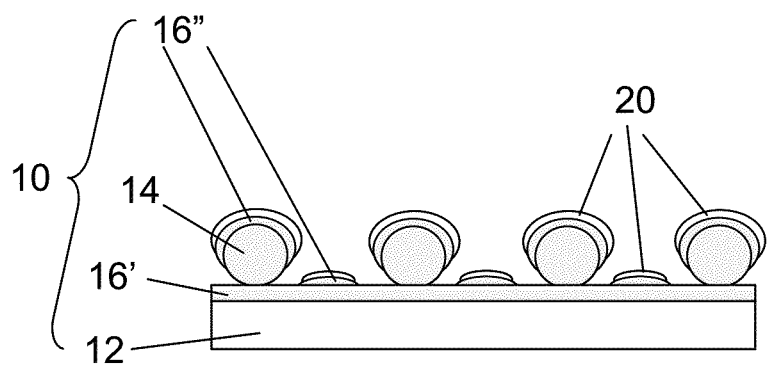
FIG. 1C is a side elevation view a SERS substrate with multiple layers of material thereon, including a first metallic coating layer, a nanostructure layer, a second metallic layer, and a plasma coating layer, according to a third embodiment of the present invention.

According to another embodiment, a novel SERS substrate 10 may include a base substrate 12, a first metallic coating layer 16', a nanostructure layer 14, a second metallic coating layer 16", and a plasma coating layer 20. As shown in FIG. 1C, the SERS surface 10 includes a base substrate 12, a first metallic layer 16', a nanostructure layer 14, a second metallic layer 16", and a plasma coating layer, where the first metallic layer 16' is deposited upon the base substrate 12, the nanostructure layer 14 is deposited upon the first metallic layer 16', a second metallic layer 16" is deposited on the nanostructure layer 14, and the last plasma coating layer 20 is then applied. A plasma coating layer 20 is deposited at least partially upon the second metallic layer 16". The first metallic layer 16' and the second metallic layer 16" may be of same or different SERS-active metals materials. The metallic coating layer 16' and 16" may be a thin film with uniform thickness, be a thin film of certain nanoroughness, or be composed of smaller nanostructures, such as nanoparticles. The materials of employed in the metallic layer 16' and 16" may be any SERS-active metallic material, such as silver, gold, copper, platinum, titanium, chromium, combinations thereof or the like. The substrate 12 may be any of the ceramic, polymer, or metal materials as described above regarding FIGS. 1A and 1B The plasma coating layer 20 may be any of the materials described above regarding FIGS. 1A and 1B.

FIG. 1A-C illustrate configuration options for multi-layered structures 10, where a plasma coating 20 may be used to either provide full or incomplete substrate coverage. Further, the plasma coating 20 may reside on the top, the bottom, or between other layers 14, 16. The nanostructures 14 may likewise either fully or incompletely cover the substrate 12. In addition to the enhanced SERS sensitivity arising from the plasma coating 20, control of the surface chemistry, the presence of multiple layers of nanostructures 14 (such as Au nanoparticles 14 positioned over an Au thin film or layer formed from smaller Au nanoparticles), and the like also may combine to improve the SERS enhancement factors.

Figure 2A:
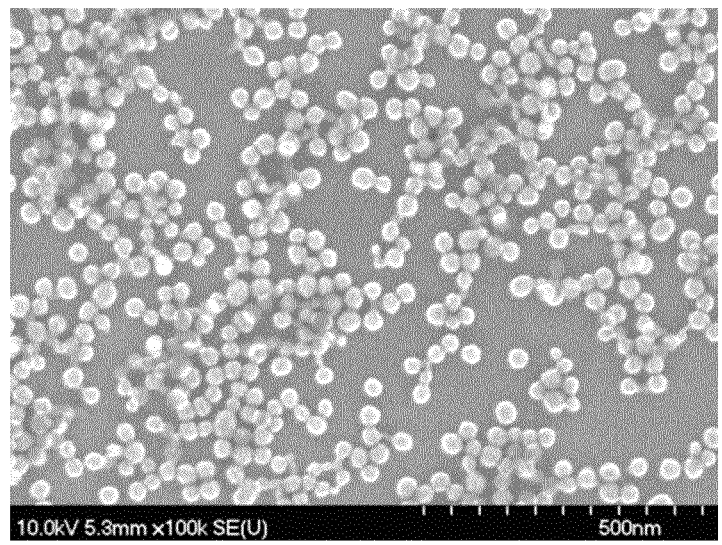
FIG. 2A is an SEM image of an exemplary nanostructure layer of an incomplete monolayer of nanoparticles.
Figure 2B:
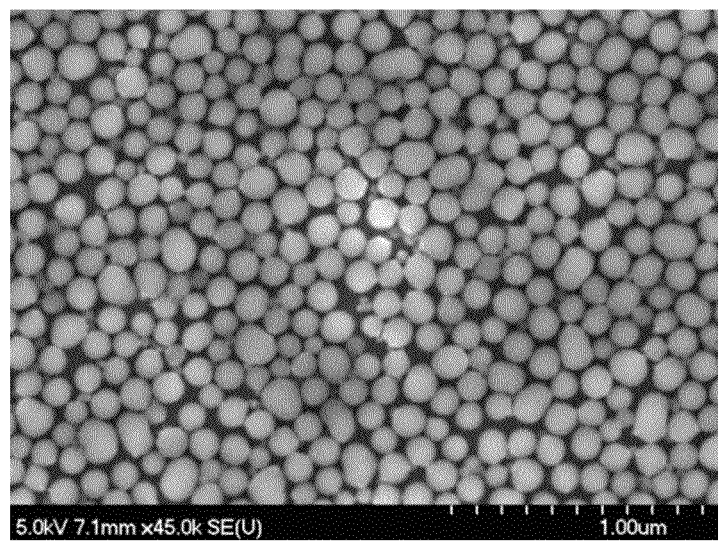
FIG. 2B is an SEM image of an exemplary nanostructure layer of a complete monolayer of nanoparticles.
Figure 2C:
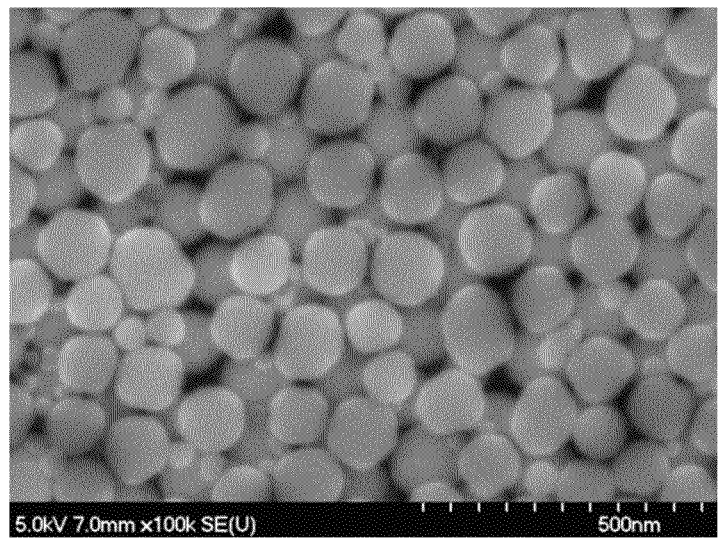
FIG. 2C is an SEM image of an exemplary nanostructure layer of a double-layer of nanoparticles.

The nanostructure layer 14 in FIG. 1B and FIG. 1C may be formed from any nanomaterials, such as nanoparticles, nanoaggregates, nanopores/nanodisks, nanorods, nanowires, or combinations thereof. The materials employed in the nanostructure layer 14 may be any ceramic, polymer, and metal materials. For example when the nanostructure layer 14 employs non-metallic nanoparticles, the nanostructure layer 14 may be deposited as an incomplete monolayer, a complete monolayer, a double-layer, or a plurality of layers, of nanoparticles, as illustrated in FIGS. 2A through 2C. FIGS. 2A-2C are SEM images of various deposition patterns of $SiO_2$ nanoparticles as deposited on the base substrate 12 (defining the nanostructure layer 14 for a respective particular embodiment). FIG. 2A is an SEM image of an incomplete monolayer of $SiO_2$ nanoparticles 14, FIG. 2B is an SEM image of monolayer $SiO_2$ nanoparticles 14, and FIG. 2C is an SEM image of a double-layer of $SiO_2$ nanoparticles 14.

Figure 3:
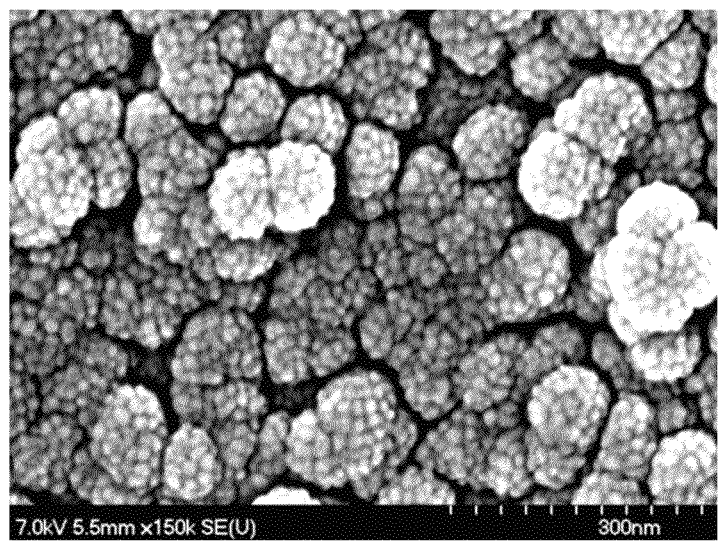
FIG. 3 is an SEM image of an exemplary nanostructure layer coated with a metallic coating layer. The metallic coating layer itself is composed of metallic nanoparticles.

The metallic coating layer 16 may be a thin film with uniform thickness, be a thin film of certain nanoroughness, or be composed of smaller nanostructures, such as nanoparticles. The materials of employed in the metallic layer 16 may be any SERS-active metallic material, such as silver, gold, copper, platinum, titanium, chromium, combinations thereof or the like. FIG. 3 is an SEM image of an $SiO_2$ nanostructure layer 14 coated with sputtered Au coating 16. In this particular case, the Au coating layer 16 is composed of Au nanoparticles, which also contribute to SERS enhancement beyond the nanostructures provided by $SiO_2$ layer 14.

Figure 4:
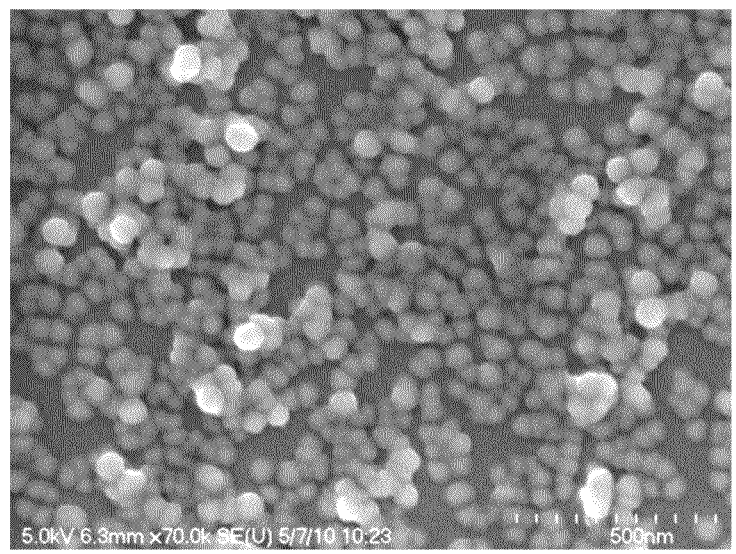
FIG. 4 is an SEM image of an exemplary SERS substrate with a layer of nanostructures, a metallic coating layer on the nanostructures, and a plasma coating on the metallic coating FIG. 5 graphically illustrates the oxygen flow rate dependence of the water surface contact angles of plasma nanocoatings, which may be applied to FIGS. 1A-1C, as obtained from a mixture of trimethylsilane (TMS) and oxygen with different gas ratios.

The plasma coating layer 20 is typically found in the present SERS substrate 10 and aids in producing the desired surface characteristics. FIG. 4 is an SEM image of an exemplary SERS substrate 10, wherein the $SiO_2$ nanoparticle layer 14 is firstly deposited upon Si wafer 12 and then coated with Au coating layer 16 followed by the plasma coating layer 20. The plasma coating layer 20 may be deposited using any convenient deposition method, such as chemical deposition. For example, according to one embodiment, low-temperature gas plasmas are partially ionized gases that are mainly produced at a reduced pressure and contain highly reactive particles including electronically excited atoms, molecules, ionic and free radical species. Depending on the plasma chemistry or gas composition, these highly reactive plasma species can clean and etch surface materials and/or bond to various substrates to form a nanoscale thin layer of plasma coating 20. Such plasma coatings 20 can be controlled in terms of coating thickness and surface characteristics such as surface chemistry, surface energy, and surface hydrophilicity by adjusting plasma conditions and/or plasma chemistry. The plasma coating thickness 20 is typically in the range of from about 1 nm to about 200 nm, with a more typical thickness range of between about 1 nm and about 50 nm.

Figure 5:
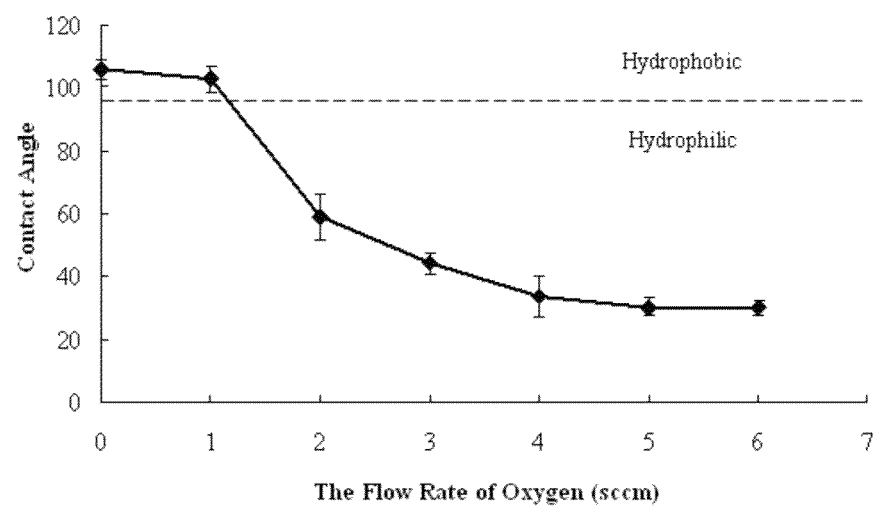

The surface energy or surface hydrophilicity of the plasma coatings 20 may be expressed by water contact angle and controllably adjusted by plasma chemistry or plasma gas composition. A smaller water contact angle corresponds to a more hydrophilic (or less hydrophobic) surface, while a larger water contact angle indicates a less hydrophilic (or more hydrophobic) surface. For example, as shown in FIG. 5, the water contact angle of the plasma coatings 20 obtained from a mixture of trimethylsilane and oxygen can be controllably adjusted from about 100 degrees to below about 40 degrees.

Figure 6:
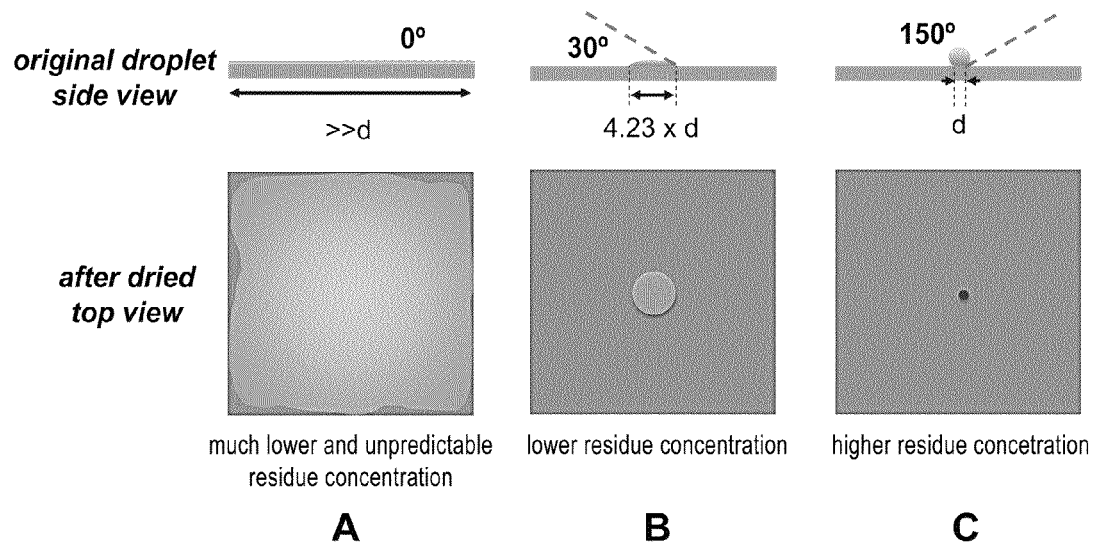
FIG. 6A graphically illustrates a first droplet on a substrate having a first contact angle and a first concentration of residue.
FIG. 6B graphically illustrates a second droplet on a substrate having a second contact angle and a second concentration of residue.
FIG. 6C graphically illustrates a third droplet on a substrate having a third contact angle and a third concentration of residue.

FIG. 6 illustrates the influence of the water contact angle on the aqueous droplet size and droplet residue size. Generally speaking, the case in FIG. 6A is not preferred as the aqueous solution spread in the SERS substrate and the size of the droplet may not be reliably controllable and the concentration of the residue is likewise difficult to predict. Such uncontrollability and unpredictability of the surface properties of the substrate 10 make SERS quantitative analysis or even to semi-quantitative analysis difficult. As shown in FIGS. 6B and 6C, with droplets having substantially the same volume, droplet residues have different sizes and concentrations. Considering a certain SERS substrate can only provide quantitative measurement for a certain chemical, such as 10 PPB-10 PPM or 1 PPM-500 PPM, it is important to control the analyte concentration in the residue. Depending on the concentration of the analyte solution, optimal conditions of surface chemistry, surface energy, water contact angle and/or hydrophilicity may be selected. For example, in order improve the limit of the detection of an analyte in aqueous solution, more hydrophobic surface with high water contact angle, leading to high concentration of the droplet residue, should be used. As another example, in order improve the limit of detection of analyte in oil solution, more hydrophilic surface with low water contact angle, which lead to high contact angle for oil and high residue concentration, may be selected. In addition, it is advantageous to keep the surface energy or water contact angle substantially uniform across a SERS substrate surface and between different SERS substrates from different batches, as the same contact angle or smaller standard deviation will lead to the same or similar residue concentration for quantitative analysis. Thus, the plasma coating layer 20 provides a means for predetermining surface characteristics selected from the group including surface energy, hydrophilicity, and contact angle with analyte solution so as to control, vary and optimize the SERS substrate 10 for a given energy source (laser type), a given analyte, and given solvent, and the like.

The water contact angles of the plasma coatings 20 are typically in the range of between about 0 degrees (very hydrophilic) to about 170 degrees (superhydrophobic), and more typically between about 80 degrees and about 140 degrees for measuring trace amount analyte in aqueous solution and about 20 degrees to about 60 degrees for trace amount analyte in organic solution. For the surface with 20-60 degree water contact angle, it is expected the contact angle for an organic solution will be over 90 degree. The typical contact angles may decrease from values over 80 degrees to values below 80 degrees for detection of aqueous samples with relatively high concentration and the typical contact angles may increase from values less than 60 degrees to values greater than 90 degrees for detection of organic samples with relatively high concentration. The controlled surface energy or hydrophilicity of the plasma coatings 20 can well confine the liquid aqueous sample area for a preselected sample volume and thus achieve consistent Raman signals for a same sample concentration. By controlling the surface energy or surface hydrophilicity of the SERS substrates, the contact area of a preselected sample volume on the substrate surface may also be controlled when organic solvents are used to prepare the sample solution, such as oil based solution, was applied. The water contact angles and detection limits between the substrate without plasma coating and the substrate with plasma coating may be compared as shown in Table 1. The results of the comparison indicate that plasma coated SERS substrate 10 had higher water contact angles, better confined the sample contact areas on the substrates, and consequently yielded improved detection limits. Moreover, the standard deviation of the contact angle also decreased after the plasma coating, which is also very beneficial for quantitative or semi-quantitative analysis, as the actual tested areas have a more constant amount of residue after evaporation. The samples with plasma coating 20 shows very consistent results on 6 inch wafers, while the samples without plasma coating show much larger variation in different locations on a 6 inch wafer.

TABLE 1

Water surface contact angles and detection limits of the Au-coated SERS substrates with and without plasma coating

| Au Coated Substrates | Water Contact Angle (standard deviation) | Detection Limits for melamine in aqueous solution |
| --- | --- | --- |
| Without plasma coating | 79° ± 12° | 250 ppb (not consistent result) |
| With plasma coating 100 ppb (consistent result) | 109° ± 4° | 100 ppb (consistent result) |

EXAMPLE 1

An aqueous colloidal suspension of $SiO_2$ nanoparticles (20-100 nm) of concentration between about 0.5%-5% may be prepared by adding a predetermined quantity of $SiO_2$ to water or by diluting high a highly concentrated colloidal suspension of $SiO_2$ with water. Magnetic stirring can be used to achieve better dispersion of the silica nanoparticles. Droplets of $SiO_2$ nanoparticle colloidal suspension may be used to coat a Si wafer, such as by using a spin coater. FIGS. 2A-2C show formation of an incomplete silica nanoparticle monolayer, a complete $SiO_2$ nanoparticle monolayer, and a double-layer $SiO_2$ nanoparticle coating, respectively, on Si wafers. After the coating process, a gold coating containing gold nanoparticles (10-20 nm) may be applied on the $SiO_2$ nanoparticle coatings. FIG. 3 shows a typical SEM image of an Au nanoparticle-coated $SiO_2$ nanoparticle coating. The Au coating thickness typically may range from 10 nm to 50 nm. After the deposition of Au coating, the substrate becomes SERS-active. Next, a plasma coating of typical thickness of 2-50 nm is then applied over the SERS-active nanosubstrates. FIG. 4 shows a typical SEM image of a plasma coated SERS-active nanosubstrate. The $SiO_2$ nanoparticles size, Au coating thickness, and the type and thickness of plasma coating may all be tailored to optimize performance for certain wavelength of laser. The plasma coating 20 may not have a uniform thickness and may not yield full coverage of the Au metal nanoparticles.

A typical application of the novel SERS substrate is for food safety applications. Recent food safety incidents involving milk and infant formula contaminated with toxic melamine have raised a great deal of concerns of consumers. Traditional analytical methods such as HPLC are time-consuming and labor-intensive, while using SERS coupled with the novel SERS substrates, melamine in foods can be detected quickly and accurately. The detection limit could reach the parts per billion (PPB) level. The SERS measurement time is typically short, typically within 15 minutes, which is much faster than traditional methods.

EXAMPLE 2

Figure 7:
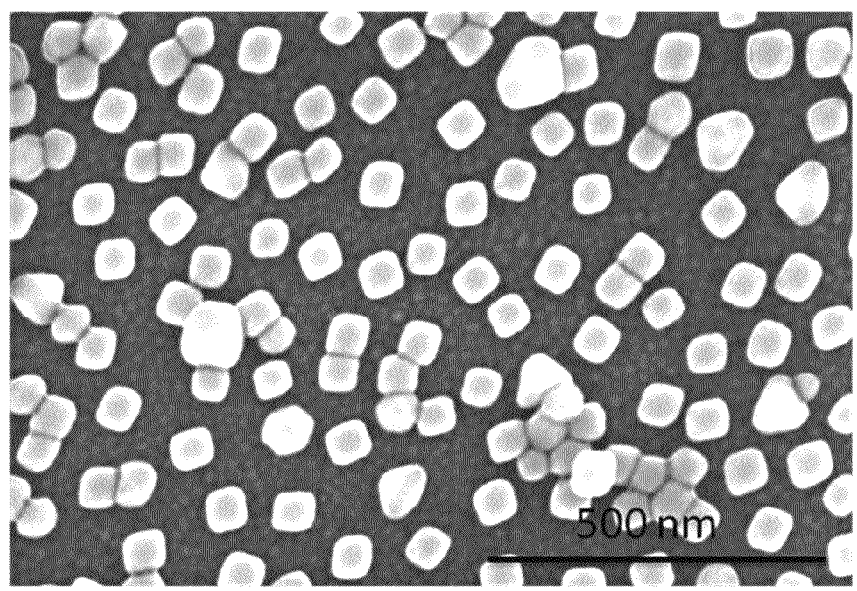
FIG. 7 is an SEM image of SERS substrates with a layer of Ag nanocubes on top of Au thin film composed of smaller Au nanoparticles.

FIG. 7 shows one example of multiple layered SERS active nanostructures 14. The first layer Au coating 16' was sputtered onto a glass substrate and a second layer Ag nanocubes 14' was dip-coated onto the Au coated glass substrate 12. Coverage of the second Ag nanocube coating 14' is controllable by concentration and/or other techniques, and the Ag nanocubes 14' may also be applied via a spin coating technique. It is expected that the Au nanoparticles 16' and Ag nanocubes 14' may work best with different laser wave lengths and may be sensitive to different chemicals. Such a combination coating may allow for the fabrication of SERS substrates 10 tailored for unique and enhanced performance and sensitivity as compared to traditional SERS substrates or even substrates 10 having uniform nanostructure layers of the same metal or metal alloy. In addition, the different nanostructures 16', 14' may interact with each other to improve the enhancement factors, such as by creating hot-spots between different layers 14', 16' of nanostructures. For example, if the top and bottom layers 14', 16' have nanostructures of significantly different sizes and/or define a significant size gap (typically over 10 nm or over 30% of the smaller one), the two layers 14', 16' may interact to substantially increase SERS sensitivity and also work for different laser wave lengths.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A surface enhanced Raman spectroscopy device, comprising:
 a base substrate;
 a first metallic nanostructure coating layer operationally connected to the base substrate;
 a nanostructure layer deposited at least partially over the first metallic nanostructure layer;
 a second metallic nanostructure coating layer deposited at least partially over the nanostructure layer; and
 a plasma deposition layer deposited at least partially over all the nanostructures on the base substrate.

2. The device of claim 1 wherein the plasma deposition layer is less than about 100 nm thick.

3. The device of claim 1 wherein the plasma deposition layer is less than about 50 nm thick.

4. The device of claim 1 wherein the nanostructure layer further comprises:
 a plurality of spaced nanostructures positioned on the base substrate;
 a plasma coating layer positioned between the spaced nanostructures.

5. The device of claim 1 wherein the plasma deposition layer has a water contact angle between about 80 and about 140 degrees.

6. The device of claim 1 wherein the plasma deposition layer has a water contact angle between about 20 and about 60 degrees.

7. The device of claim 1 wherein the plasma deposition layer has a water contact angle between about 60 and about 90 degrees.

8. A surface-enhanced Raman spectroscopy substrate device, comprising:
 a substrate;

a plurality of nanostructures disposed on the substrate to define a nanostructure layer;
a metallic coating layer deposited at least partially over the nanostructure layer; and
a plasma deposition layer at least partially covering the nanostructure layer;
wherein the nanostructure layer includes a plurality of features sized between about 20 and about 200 nanometers across;
wherein the metallic coating layer is made up of at least one of the group including gold, silver, platinum, titanium, chromium, silica and combinations thereof;
wherein the metallic coating layer is at least about 10 nanometers thick;
wherein the plasma deposition layer is less than about 100 nanometers thick; and
wherein the plasma deposition layer has a water contact angle between about 20 and about 140 degrees.

9. The surface-enhanced Raman spectroscopy substrate device of claim 8 and further comprising a second metallic layer at least partially covering the base substrate.

\* \* \* \* \*